United States Patent [19]
Kramer et al.

[11] Patent Number: 6,080,417
[45] Date of Patent: Jun. 27, 2000

[54] HAND DISINFECTANT

[75] Inventors: Axel Kramer; Leopold Döhner, both of Greifswald, Germany

[73] Assignee: Antiseptica Chemisch-Pharmazeutische Produkte GmbH, Germany

[21] Appl. No.: 08/952,685

[22] PCT Filed: Jan. 31, 1997

[86] PCT No.: PCT/EP97/00417

§ 371 Date: Aug. 31, 1998

§ 102(e) Date: Aug. 31, 1998

[87] PCT Pub. No.: WO97/35475

PCT Pub. Date: Oct. 2, 1997

[30] Foreign Application Priority Data

Mar. 27, 1996 [DE] Germany ............ 196 12 057

[51] Int. Cl.[7] .......... A01N 25/00; A01N 31/00; A01N 41/10; A61K 31/075
[52] U.S. Cl. .......... 424/405; 424/400; 424/616; 514/706; 514/709; 514/714
[58] Field of Search .............. 424/400, 405, 424/616; 514/706, 709, 714

[56] References Cited

U.S. PATENT DOCUMENTS

| | | |
|---|---|---|
| 4,900,721 | 2/1990 | Bansemir et al. . |
| 5,043,357 | 8/1991 | Hoffler et al. . |
| 5,122,541 | 6/1992 | Eggensperger et al. . |
| 5,213,803 | 5/1993 | Pollock . |
| 5,411,598 | 5/1995 | Tsao . |
| 5,591,442 | 1/1997 | Diehl et al. . |

FOREIGN PATENT DOCUMENTS

| | | |
|---|---|---|
| 1318247 | 5/1993 | Canada . |
| 0 251 303 | 1/1988 | European Pat. Off. . |
| 0 252 278 | 1/1988 | European Pat. Off. . |
| 0 384 126 | 8/1990 | European Pat. Off. . |
| 2 231 496 | 11/1990 | European Pat. Off. . |
| 0 547 727 | 6/1993 | European Pat. Off. . |
| 0 689 767 | 1/1996 | European Pat. Off. . |
| 0 689 768 | 1/1996 | European Pat. Off. . |
| 1492024 | 2/1969 | Germany . |
| 29 04 217 | 8/1980 | Germany . |
| 31 17 792 | 11/1982 | Germany . |
| 37 23 990 | 2/1988 | Germany . |
| 3725381 | 2/1988 | Germany . |
| 29514293 | 1/1996 | Germany . |
| 19532884 | 3/1997 | Germany . |
| WO 93/07250 | 4/1993 | WIPO . |
| WO 95/02393 | 1/1995 | WIPO . |
| WO 97/35475 | 10/1997 | WIPO . |

OTHER PUBLICATIONS

International Search Report, PCT/EP 97/00417, May 15, 1997.

Primary Examiner—S. Mark Clardy
Assistant Examiner—Kathryne E. Shelborne
Attorney, Agent, or Firm—Pillsbury, Madison & Sutro LLP

[57] ABSTRACT

The invention concerns a hand disinfectant based on lower alcohols and is characterized by an aqueous solution of lower alcohols with synergists, the solution having a flash point of more than 21° C.

11 Claims, No Drawings

HAND DISINFECTANT

Hand disinfectants containing one or more lower alcohols, such as ethanol, isopropanol or n-propanol, are widely known. As a rule, they are aqueous solutions with an alcohol content of 70 to 80 weight %, and optionally other compounds that have microbicidal action are added. These known hand disinfectants meet the requirements, formulated by DGHM, for the germicidal effect against bacteria, including mycobacteria, and fungi.

Increasingly, the viral effectiveness of hand disinfectants based on alcohol has lately been discussed. Their virus inactivation, particularly against highly resistant types of virus, such as polio, does not meet all demands; for instance, it is known that polio viruses for instance can be inactivated only with a very high percentage of ethanol, and so the usual concentration of between about 70 and 80 weight % is not adequate for this purpose. Hence hand disinfectants based on 90 to 95 weight % ethanol are already on the market. Although these disinfectants meet the demands for virus inactivation made by the DVV, they have some decisive disadvantages. The most important disadvantage is that the flash point of such mixtures with a high ethanol content is below 21° C., which makes the preparations subject to the Code on Flammable Liquids in hazard class B1, and special regulations must be obeyed regarding shipping, storage, bottling, and the like. This is a particular burden for hospitals and large medical practices, because large quantities of disinfectants are needed, and in general the supply rooms of the applicable institution are not set up for storing relatively large quantities of flammable liquids. Another disadvantage is that disinfectants with such a high alcohol content, when used for disinfecting hands, dry the skin to an extraordinary degree, with all the attendant, well-known side effects.

There is therefore still an urgent need for hand disinfectants with good virus inactivation effectiveness even for known resistant types of virus, but which do not come under hazard class B1 of the Code on Flammable Liquids and which moreover are readily tolerated.

To attain this object, hand disinfectants on the basis of lower alcohols are proposed, which are characterized in that they contain lower alcohols together with synergists in an aqueous solution and have a flash point above 21° C.

Surprisingly, it has been found that instead of the previously conventional high-percentage ethanol solutions for viricidal hand disinfection, preparations that have a substantially lower alcohol content in the form of lower alcohols can also be used, if they contain mixtures of synergists that promote the viricidal action or virus inactivation of the alcohols, and hence mixtures can be prepared that are no longer in hazard class B1 of the Code on Flammable Liquids. Those whose use is preferred are the lower alcohols, that is, ethanol, isopropanol or n-propanol, which in high concentration have flash points below 21° C., but which are preferably used in such an aqueous solution that the total alcohol content is between about 50 and 60 volume %.

To increase the viricidal or virus-inactivating action, diols are used, specifically preferably those with a chain length of from 3 to 5 carbon atoms. Propanediols are especially suitable, and both positional isomers, that is, 1,2-propanediol and 1,3-propanediol can be used. 1,2-Propanediol is considered safe, although recent studies have indicated that the toxicity may be somewhat higher than in the 1,2-isomer. Along with the propanediols, butanediols can also be considered, and specifically all the positional isomers, but 1,3-butanediol is preferred, because the most toxicological data is available for it.

The diols have a certain bacteriostatic action, and moreover they are used in the foods industry against fungi, for example, and especially against yeasts. The concentration of the diols may be low and ranges from about 3 to about 10 volume Besides the diols, other additives can also be considered, specifically hydrogen peroxide in a 1 to 3% concentration and sodium alkane sulfonates (E30), that is, essentially secondary sulfonic acids with a chain length of the alkyl group of between about 12 and 18 carbon atoms. Alkane sulfonates are environmentally tolerable anionic surfactants which exhibit a strong virus-inactivating effect. The concentration of the alkane sulfonates is in the range frog about 0.2 to about 0.7 weight %.

The substance known as sodium rhodanide, NaSCN, is another highly effective synergistic compound. It is indeed known that thiocyanic acid and its salts are microbicidally effective, but so far this activity has hardly been utilized for disinfecting purposes. The concentration of rhodanide should be between about 1 and 3 weight %.

The mixtures according to the invention are adjusted to be acidic, which can be done by adding physiologically safe organic acids that are easy on the skin, in a concentration of about 0.001 to 0.005 mole %. Preferably, citric acid, tartaric acid, malonic acid or malic acid is used, because these acids have no odor of their own. However, other toxigologically unobjectionable acids may also be used, such as lactic acid, acetic acid, formic acid or propionic acid, and similar compounds.

The mixtures according to the invention have flash points above 21° C. and are therefore not subject to the more-stringent requirements made of substances in hazard class B1. They are markedly easier on the skin than preparations with a very high content of alcohols, because drying of the skin does not ensue to the same degree as with high-alcohol solutions. Their effectiveness against bacteria, yeasts and fungi meets the regulations of the DVV or of BIFAM. But in terms of virus-inactivating effectiveness, they also meet the requirements of the DGHM.

The preparation of the disinfectants of the invention is done in a manner known per se, by dissolving the usually solid organic acids and by dissolving the synergistically active compounds, such as alkane sulfonates or rhodanide, in some of the total amount of water needed, mixing the liquid alcohols, and adding the total amount of water needed.

The invention will be described in further detail below in terms of the Examples:

EXAMPLE 1

6 l of 96% ethanol are mixed with 500 ml of 1,2-propanediol and 500 ml of 1,3-butanediol and mixed carefully. Into this mixture, an aqueous solution of 200 ml of 1-molar citric acid is worked in, and the mixture is then diluted with 2.8 l of double-distilled water. The flash point, determined in accordance with DIN 51755, is 22.5° C.

EXAMPLE 2

6 l of 96% ethanol, as indicated in Example 1, are mixed with 500 ml of 1,2-propanediol and 500 ml of 1,3-butanediol and 200 ml of a 1-molar tartaric acid solution and diluted with 2.8 l of distilled water. The flash point, determined in accordance with DIN 51755, is 23.0° C.

EXAMPLE 3

As described in Example 1, 6 l of 96% ethanol, 1 l of 1,2-propanediol, 1 l of 1,3-butanediol and 200 ml of a 1-molar citric acid are mixed and water is added to make up 10 l.

EXAMPLE 4

6 l of 96% ethanol, 3 l of 1,2-propanediol, and 200 ml of 1-molar malic acid are mixed and water is added to make up 10 l.

EXAMPLE 5

6 l of 96% ethanol are mixed with 1 l n-propanol, 500 ml of 1,2-propanediol and 500 ml of 1,3-butanediol and mixed carefully. Into this mixture, an aqueous solution of 200 ml of 1-molar citric acid is worked in, and the solution is then diluted with 1.8 l of double-distilled water.

The flash point, determined in accordance with DIN 51755, is 22° C.

EXAMPLE 6

6 l of 96% ethanol are mixed with 500 ml n-propanol, 500 ml of isopropanol, 500 ml of 1,2-propanediol and 500 ml of 1,3-butanediol and mixed. Into this mixture, 200 ml of a 1-molar malic acid solution is then worked in, and the solution is then diluted with 1.8 l of double-distilled water.

The flash point, determined in accordance with DIN 51755, is 21.5° C.

EXAMPLE 7

6 l of 96% ethanol are mixed with 200 ml n-propanol, 700 ml isopropanol, 500 ml of 1,2-propanediol and 500 ml of 1,3-butanediol and mixed. Into this mixture, 200 ml of 1-molar citric acid is then worked in, and the solution is then diluted with 1.9 l of double-distilled water.

The flash point, determined in accordance with DIN 51755, is 21° C.

We claim:

1. A hand disinfectant based on lower alcohols which comprises an aqueous solution of lower alcohols along with one or more diols and one or more synergists selected from the group consisting of hydrogen peroxide, alkane sulfonates and salts of thiocyanic acid, said disinfectant having a flash point above 21° C.

2. The hand disinfectant of claim 1 which contains ethanol.

3. The hand disinfectant of claim 2 which has an ethanol content between about 50 and about 60 volume %.

4. The hand disinfectant of claim 3 which has an ethanol content of about 57 volume %.

5. The hand disinfectant of claim 1 which contains propanediol.

6. The hand disinfectant of claim 1 which contains butanediol.

7. The hand disinfectant of claim 1 which contains 1,2-propanediol.

8. The hand disinfectant of claim 1 which contains 1,3-butanediol.

9. The hand disinfectant of claim 1 which contains approximately 5–10 volume % diols, 1–3 weight % hydrogen peroxide or salts of thiocyanic acid, and/or 0.2 to 0.7 weight % alkane sulfonates.

10. The hand disinfectant of claim 1 which contains at least one physiologically safe organic acid.

11. The hand disinfectant of claim 1 which contains between about 0.01 and 0.05 mole % organic acids.

* * * * *

UNITED STATES PATENT AND TRADEMARK OFFICE
CERTIFICATE OF CORRECTION

PATENT NO.      : 6,080,417
DATED           : June 27, 2000
INVENTOR(S)     : KRAMER, Axel and DOHNER, Leopold It is certified that error appears in the above-identified patent and that said Letters Patent is hereby corrected as shown below:

Column 4, line 31, please change "about 0.01 and 0.05 mole % organic acids" to --about 0.001 and 0.005 mole % organic acids--.

Signed and Sealed this

Eighth Day of May, 2001

Attest:

NICHOLAS P. GODICI

*Attesting Officer*      *Acting Director of the United States Patent and Trademark Office*